United States Patent
Mollenhauer et al.

(10) Patent No.: US 6,666,066 B1
(45) Date of Patent: Dec. 23, 2003

(54) DEVICE FOR EXAMINING FRICTION CONDITIONS

(75) Inventors: Olaf Mollenhauer, Ilmenau (DE); Matthias Scherge, Manebach (DE); Andreas Karguth, Gotha (DE)

(73) Assignee: Tetra Gesellschaft für Sensorik, Robotik und Automation mbH, Ilmenau (DE)

( * ) Notice: Subject to any disclaimer, the term of this patent is extended or adjusted under 35 U.S.C. 154(b) by 0 days.

(21) Appl. No.: 09/647,436

(22) PCT Filed: Mar. 31, 1999

(86) PCT No.: PCT/DE99/00981
§ 371 (c)(1),
(2), (4) Date: Nov. 21, 2000

(87) PCT Pub. No.: WO99/51965
PCT Pub. Date: Oct. 14, 1999

(30) Foreign Application Priority Data

Apr. 3, 1998 (DE) .......................... 198 14 911

(51) Int. Cl.$^7$ ............................................. G01N 19/02
(52) U.S. Cl. ............................................................ 73/9
(58) Field of Search .............................. 73/9, 105, 106; 250/306, 307

(56) References Cited

U.S. PATENT DOCUMENTS

| | | | |
|---|---|---|---|
| 4,646,557 A | * 3/1987 | Park .............................. | 73/9 |
| 5,115,664 A | * 5/1992 | Hedge et al. ................... | 73/9 |
| 5,212,657 A | * 5/1993 | Uchikawa et al. ............. | 702/42 |
| 5,377,525 A | * 1/1995 | Hutchinson et al. ........... | 73/9 |
| 5,400,661 A | 3/1995 | Cook et al. ................. | 73/862.43 |
| 5,661,235 A | 8/1997 | Bonin .......................... | 73/105 |
| 5,908,981 A | * 6/1999 | Atalar et al. ................... | 73/105 |

OTHER PUBLICATIONS

Burger J F et al: "Miniaturised Friction Force Measuring System for Tribological Research on Magnetic Storage Devices" Proceedings of the 9$^{th}$. Annual International Workshop on Micro Elec Mechanical Systems, Investigation of Micro Structures, Sensors, Actuators, Machines and Systems, San Diego, Feb, 11–15, 1996 No. Workshop 9, Feb. 11, 1996, pp. 99–104 XP000689253.

"Measuring Adhesion and Friction Forces" NTIS Tech Notes, May 1, 1991, pp. 422 XP000234548 ISSN: 0889–8464 middle column; figure 2.

Mittmann H U et al: "Reibungsmessungen und Oberflächenuntersuchungen an Kunststoff–Metall Gleitpaarungen" Materialprüfung, vol. 17, No. 10, Oct. 1975, pp. 366–367, XP002112539 Düsseldorf, DE cited in the application p. 367, middle column, paragraph 2—right hand column, paragraph 1; figure 2.

* cited by examiner

Primary Examiner—Helen Kwok
Assistant Examiner—David Rogers
(74) Attorney, Agent, or Firm—Collard & Roe, P.C.

(57) ABSTRACT

The aim of the invention is to provide a device for measuring friction conditions enabling precise measurement and displaying high reproductibility, using simple means. According to the invention, this is achieved by connecting the point of application of force for the introduction of a normal force to the point of application of force of a normal force sensor by means of an elastic flexing element. The flexing element is also connected to the point of application of force for the introduction of a tangential force and the friction force sensor. Connections occur via partial areas with varying flexural strengths and both partial areas are offset at an angle of 90°. The inventive device which examines the friction conditions between friction partners enables a normal force to be applied between two corresponding friction partners and to be determined by means of a normal force sensor. The tangential force that also acts between the corresponding friction partners is determined using a friction force sensor.

8 Claims, 4 Drawing Sheets

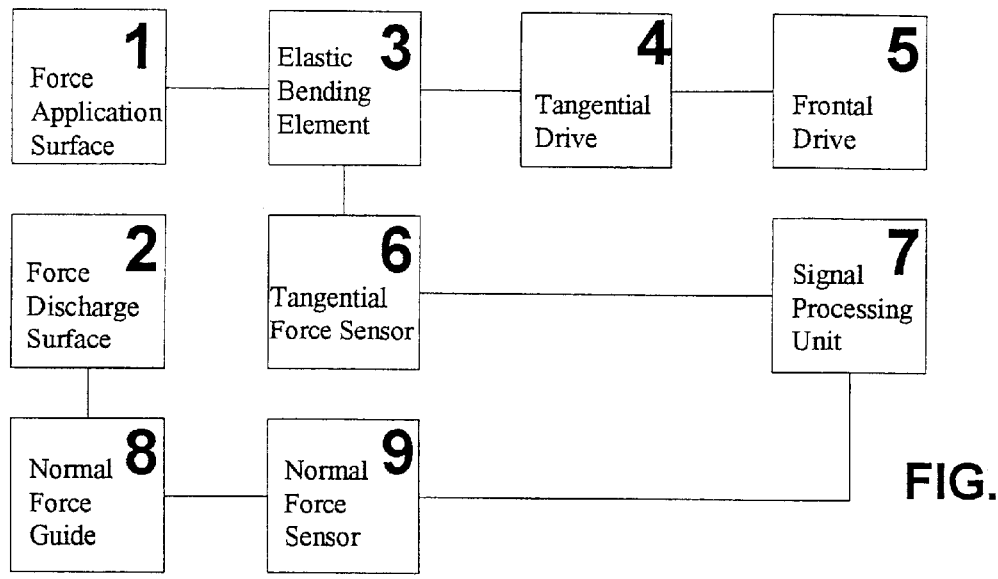
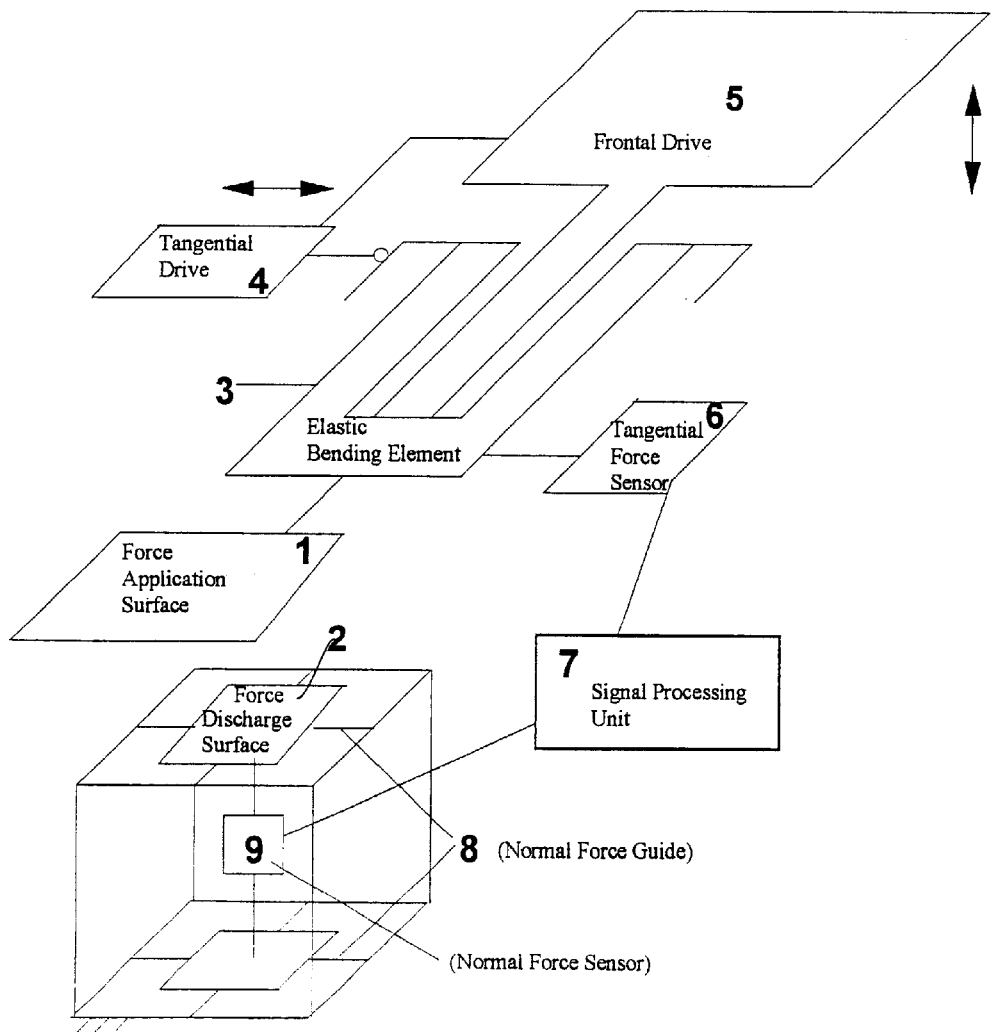

DEVICE FOR EXAMINING FRICTION CONDITIONS

BACKGROUND

The invention relates to a device for examining friction conditions on friction partners, by which a normal force is impressed between two friction partners to be tested, and determined by means of a normal force sensor, and by which, furthermore, the tangential force acting during a relative movement between the friction partners is determined by means of a friction force sensor.

The device serves for determining low friction values with high accuracy.

Different designs of devices for exactly testing friction conditions are known in the prior art.

A device designed in the form of a pin-and-disk tribometer is described in MITTMANN, CZICHOS: Friction Measurements and Surface Examinations on Plastic/Metal Sliding Partners; Materialprüfung 17, 1975, No. 10, October, pages 366–367. The tests are carried out in that connection in a closed test chamber that can be tempered and flushed with defined gases. The disk is driven at constant speed by a tachometer-controlled dc motor via an interconnected gearing. A cylindrical pin made of Polytetrafluorothylene (PTFE), High Density Polyethylene (HDPE) or Polyethylene Terephthalate (PETP) is cut prior to the test with a microtome. The pin is aligned parallel with the surface of the disk with a pair of observation binoculars. An arrangement comprising four flexing spars is employed as the element absorbing the force.

The drawback in this connection is that the device requires much expenditure and that it can be used only within a limited range of forces.

A device for testing friction conditions, in which tangential and normal forces are transmitted with an elastic flexural element, is known from BURGER J F ET AL, Proc. 9$^{th}$ Annual Workshop on Micro mechanical Systems, San Diego 1996 (IEEE), pp 99 to 104.

A force sensor for instruments used in surface analysis is known from U.S. Pat. No. 5,661,235, where biaxial spring elements are employed for transmitting tangential and normal forces.

The known arrangements have the drawback that they either require a costly structure or permit only low measuring accuracy.

SUMMARY

Therefore, the invention is based on the problem of proposing a device of the type specified above that permits measurements with high accuracy and good reproducibility with simple means.

In a preferred embodiment of the invention, the device has an elastic flexing element made of glass, which contains a plurality of spring arrangements with different spring stiffness properties. Integrated in the elastic element is a soft parallel spring element, which is provided with stops that are integrated in the elastic element for impressing the tangential movement, and a harder leaf spring element for impressing the normal force, the leaf spring element acting perpendicular in relation to the two parallel spring elements.

The points of application of force and the sensors are located in each case)on opposite parts of the elastic flexing element.

Using a frontal drive, a motion is generated in the direction of the area normal to the friction surfaces that are in contact with one another. An adjusting device is usefully integrated in the frontal drive for aligning the two body planes in parallel. The deflection of the relatively hard (horizontal) part of the elastic flexing element, such deflection being generated by the movement of the frontal drive, has the effect that the two friction surfaces will be disposed one on top of the other with an adjustable, exactly measurable, and low normal force (ranging from a few $\mu$N to about 10 N). The normal force is converted into an electrical signal with a force sensor, preferably by means of an optical distance sensor. For the determination of the friction conditions it is necessary to determine the force acting tangentially. A relative movement is impressed for said purpose with the tangential drive. The soft elastic tangential guide and the application of force connected therewith ensue not directly in dependence of the friction conditions from the driving force, but rather from a difference in the distance obtained between the part of the elastic tangential guide connected to the point of application of the forcer and the part of the tangential guidance connected to the tangential drive. Said difference in distance is converted into an electrical signal with the help of a sensor, preferably by means of an optical distance sensor, and supplied to a signal processing unit together with the signal from the normal force sensor.

BRIEF DESCRIPTION OF THE DRAWINGS

The invention is explained in greater detail in the following with the help of an exemplified embodiment. In the associated drawings, FIG. 1 is a block diagram for explaining the basic structure of the measuring arrangement.

FIG. 2 is a functional diagram of the measuring arrangement.

DETAILED DESCRIPTION

Figure 3:
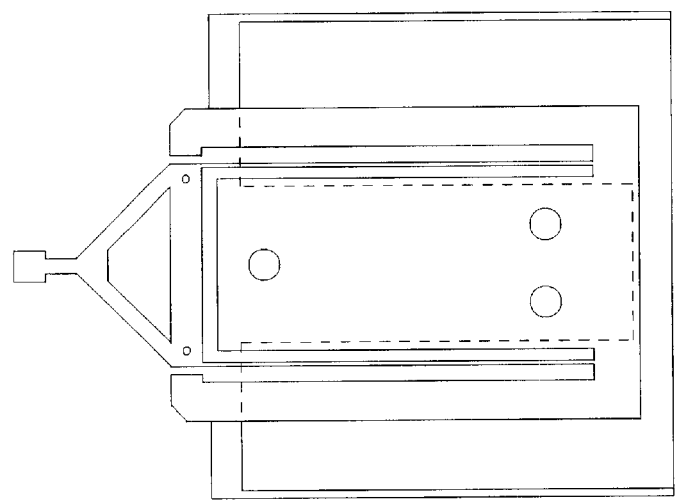
FIG. 3 is a top view of the elastic element.

The block diagram represented in FIG. 1 shows the individual functional elements of the measuring arrangement and the way in which said elements interact.

FIG. 2 explains the method in which the measuring arrangement functions. The friction surfaces are in touch with one another with the force-application surface 1 and the force discharge surface 2. A normal force is impressed between the friction surfaces. For this purpose, a frontal movement extending in the horizontal direction is generated by means of the frontal drive 5. An adjustment device (not shown) is integrated in the frontal drive 5, which allows parallel alignment of the two friction surfaces 1 and 2. The normal force causes an elastic deflection of the elastic bending element 3 that acts at the same time as the normal force guide 8. The normal force is determined by means of a normal force sensor 9, which preferably is designed in the form of an optical distance sensor. The sensor generates an electrical signal that can be interpreted.

The relative movement required for determining the fractional properties between the friction surfaces 1 and 2 is impressed with the tangential drive 4. This causes the elastic bending element 3 and the force application surface 1 to be moved in such a way that, depending on the friction conditions, the elastic bending element 3 cannot directly follow the driving motion as a function of the friction conditions.

The difference in distance between the part of the elastic bending element 3 connected with the force application surface 1, and the part of the elastic bending element 3 connected with the tangential drive is a measure of the friction conditions to be determined, and depends on its elastic properties and the normal force impressed. The difference in distance is converted into an electrical signal by means of a tangential force sensor 6, which preferably is an optical distance sensor as well, and supplied to a signal processing unit 7 together with the signal from the normal force sensor 9. The force discharge surfaces 2 is coupled with the normal force sensor 9 via a normal force guide 8.

Figure 4:
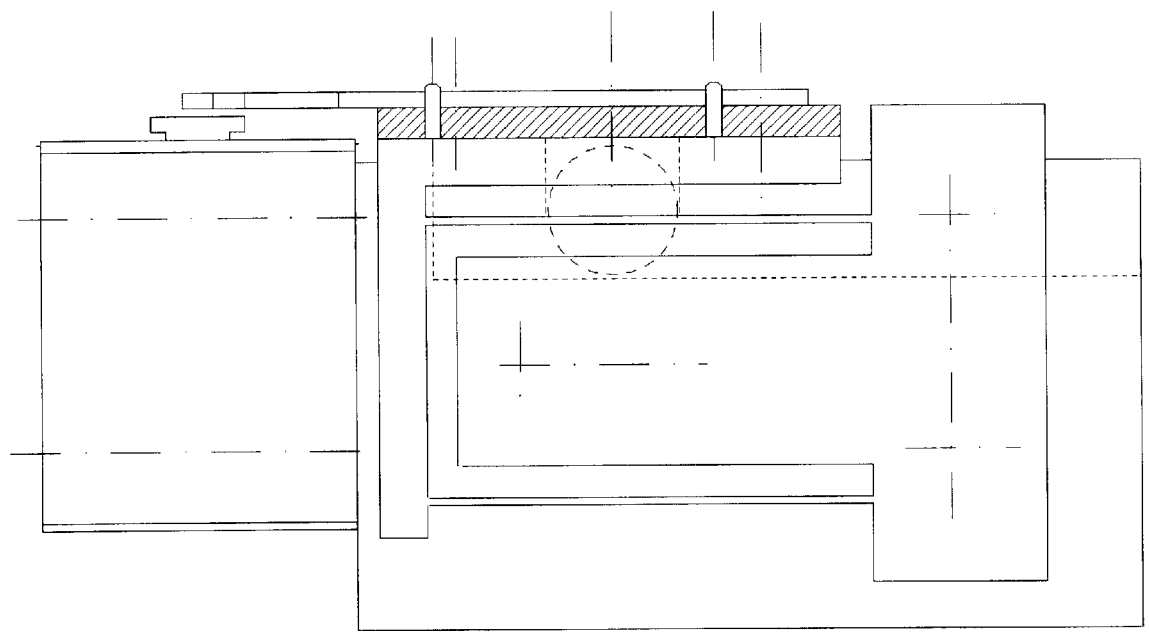
FIG. 4 is an overall view of the measuring arrangement.

FIG. 3 shows the embodiment of the elastic element 3, and FIG. 4 explains a variation of the measuring arrangement shown by a side view.

The functional structure for the elastic bending element employed for the arrangement, as defined by the invention, is a force-absorbing element for measuring very low forces. The elastic bending element consists of a glass part having a structure that takes into account both the technical material properties of the glass, which can be structured, and the manufacturing technology, such as etching.

The elastic bending element formed of structured glass as defined by the invention offers substantial advantages over other deformable elements produced by other manufacturing methods and from other materials. In addition to the advantage of free geometric shaping of functional elements in the smallest of sizes, this includes in particular the advantage that the functional plane can be arranged in the planes of the starting material.

Figure 5:
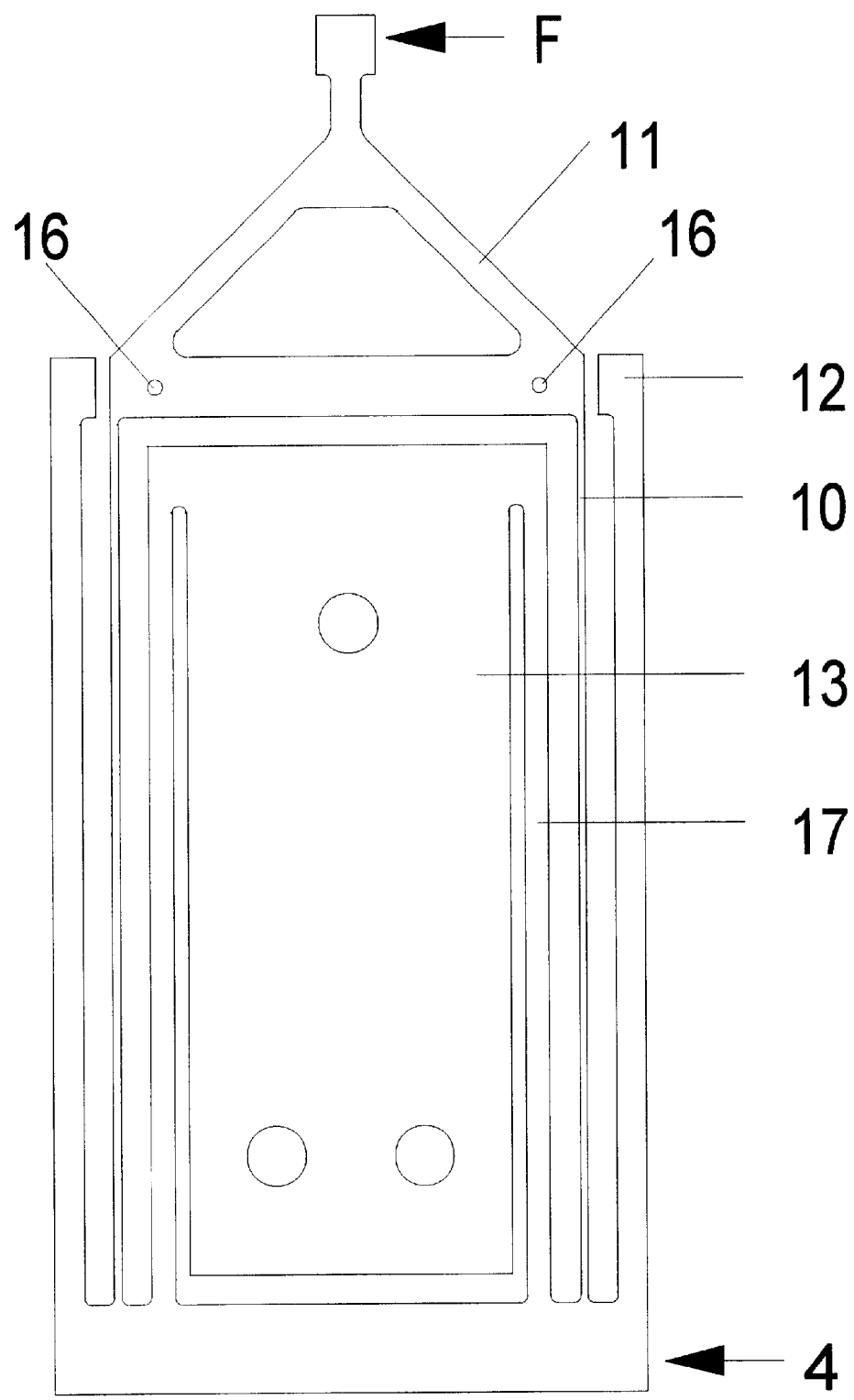
FIG. 5 shows two embodiments of the elastic element.

FIG. 5 shows a possibility for designing a micro-sized force-absorbing element. In said arrangement, the two soft bending springs 10 are connected via the coupling element 11 to form a system with parallel springs. The deflection of the parallel-spring arrangement is a measure for the tangential force "F". The coupling element 11, when employed as a force-measuring system, serves for impressing the force "F" into the plane of the glass. The distance of deformation is limited by the side elements 12. The connection to the rack is established via the connecting surface 13. The stiffer tangential guide 17, which represents a parallel spring arrangement as well, serves for guiding the bending springs 10 when paths are impressed by the tangential drive.

It is possible, with said arrangement, to achieve high reproducibility of the individual geometric values of the micro force-absorbing element.

It was possible within the framework of the testing of different structures to demonstrate that a measurement and form tolerance of 10 $\mu$m is maintained even with larger dimensions. This corresponds with a relative error of about 0.15% to 0.2%.

Figure 6:
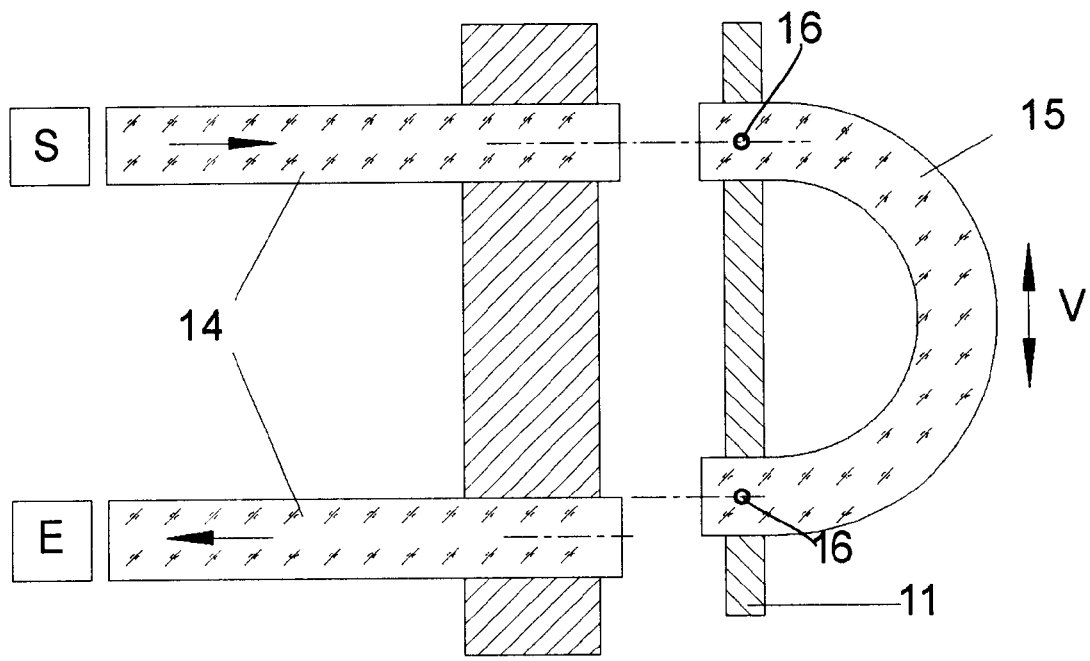
FIG. 6 shows the principle of the fiber-optic force measuring arrangement.

FIG. 6 shows the principle of the fiber-optical force measurement arrangement, which is integrated in the elastic bending element and serves for measuring the tangential force via the displacement V of the coupling element 11 with the connection body 15. The radiation generated by the emitter "S" is conducted via a light wave conductor 14 to the outlet opening from where such radiation is emitted.

The connecting body 15, which is seated on the coupling element 11 of the parallel spring arrangement, passes the rays on and becomes an emitter at its other end as well. The rays are absorbed by the light-conducting body 14, which is connected to the receiver "E", and converted into an electrical signal. The light-conducting body 14 is preferably a light wave conductor. The inlet and outlet openings serve as shutters.

Said arrangement permits using the linear range of the characteristic with high sensitivity, as well as targeted suppression of the influence of interfering quantities. The light-conducting connecting body 15 is secured in the two breakthroughs 16 of the coupling element 11. It was possible to detect the deflection caused by the force application "F" with an accuracy of about 100 nm. The resolution limit is at about 10 nm.

The result of the above is an arrangement for measuring micro-forces with a resolution of about 0.1 $\mu$N. The arrangement as defined by the invention permits a measuring range for micro-force measurements of from 10 $\mu$N to 100 $\mu$N.

REFERENCE NUMERALS AND LETTERS

1 Force application surface
2 Force discharge surface
3 Elastic bending element
4 Tangential drive
5 Frontal drive
6 Tangential force sensor
7 Signal processing unit
8 Normal force guide
9 Normal force sensor
10 Spiral spring
11 Coupling element
12 Side element
13 Connecting surface
14 Light wave guide
15 Connecting body
16 Perforation
17 Tangential guide
F Force application
E Receiver of light radiation
S Emitter of light radiation
V Displacement

What is claimed is:

1. A device for examining friction conditions of friction partners wherein a normal force is pressed between two friction partners and then determined using a normal force sensor, the device comprising:

a) at least one elastic bending element having a first end for receiving a normal force and a second end, said at least one elastic bending element comprising:
  i) a first set of two parallel spaced springs extending in a straight manner along a longitudinal axis in a first direction;
  ii) a second set of two parallel spaced springs having a higher stiffness than said first set of two parallel spaced springs and extending parallel to said first set of two parallel spaced springs;

b) a tangential drive coupled to said second end of said at least one elastic bending element;

c) a tangential force sensor coupled to said at least one elastic bending element to determine a path difference between said first end of said at least one elastic bending element that receives the normal force and said second end of said at least one elastic bending element connected to said tangential drive;

d) at least one frontal drive coupled to said at least one elastic bending element, wherein said frontal drive generates a frontal movement that runs in a horizontal direction; and e) at least one signal processing unit in communication with said tangential force sensor and the normal force sensor wherein said signal processing unit receives signals from said tangential force sensor and the normal force sensor to determine the friction condition of the friction partners.

2. The device as in claim 1, further comprising at least one coupling element for coupling said first and said second set of said two parallel spaced springs together, said coupling element extending in a direction offset by 90° from the direction of extension of said first and said second set of two parallel spaced springs.

3. The device as in claim 1, wherein said second se of parallel spaced springs allows the introduction of tangential movement and are disposed between said first partial region and an introduction point of said normal force.

4. The device as in claim 1, further comprising a plurality of stops coupled to said at least one elastic bending element for limiting a linear movement of said first set of said two parallel spaced springs.

5. The device as in claim 1, wherein said elastic bending element is made from etched glass.

6. The device as in claim 1, wherein said at least one frontal drive introduces a normal force, and wherein said at least one frontal drive comprises an adjusting device for aligning two different planes of contact of said first set of two parallel spaced springs and said second set of parallel spaced springs in parallel.

7. The device as in claim 1, wherein the normal force sensor and said friction force sensor are each optical distance sensors that convert output signals into electrical signals which are sent to said at least one signal processing unit.

8. The device as in claim 1, further comprising at least one fiber optic component coupled to said at least one elastic bending element and wherein said tangential force sensor is an optical sensor in communication with said fiber optic component.

* * * * *